United States Patent
Hsieh et al.

(10) Patent No.: US 10,011,646 B2
(45) Date of Patent: Jul. 3, 2018

(54) RECOMBINANT DECOY RECEPTOR 3 FOR TREATING SPINAL CORD INJURY

(71) Applicant: Academia Sinica, Taipei (TW)

(72) Inventors: Shie-Liang Hsieh, Taipei (TW);
Henrich Cheng, Taipei (TW);
Wen-Hung Huang, Taipei (TW);
Chuan-Wen Chiu, Taipei (TW);
Shao-Ji Lin, Taipei (TW)

(*) Notice: Subject to any disclaimer, the term of this patent is extended or adjusted under 35 U.S.C. 154(b) by 0 days.

(21) Appl. No.: 15/239,971

(22) Filed: Aug. 18, 2016

(65) Prior Publication Data

US 2017/0051038 A1 Feb. 23, 2017

Related U.S. Application Data

(60) Provisional application No. 62/206,405, filed on Aug. 18, 2015.

(51) Int. Cl.
| | |
|---|---|
| *A61K 38/17* | (2006.01) |
| *A61K 39/395* | (2006.01) |
| *C07K 14/705* | (2006.01) |
| *A61K 9/00* | (2006.01) |

(52) U.S. Cl.
CPC ...... *C07K 14/70578* (2013.01); *A61K 9/0019* (2013.01); *A61K 9/0085* (2013.01); *A61K 38/1793* (2013.01); *A61K 39/3955* (2013.01); *C07K 2319/30* (2013.01)

(58) Field of Classification Search
CPC .. A61K 38/17; A61K 38/1774; A61K 38/191; A61K 47/48415
See application file for complete search history.

*Primary Examiner* — Robert C Hayes

(57) ABSTRACT

Disclosed herein are methods for treating spinal cord injury using recombinant decoy receptor 3 (DcR3) polypeptide. Also disclosed herein are methods for improving the locomotor function recovery of a spinal cord injured subject with a DcR3 polypeptide.

9 Claims, 11 Drawing Sheets
(7 of 11 Drawing Sheet(s) Filed in Color)

SEQUENCE LISTING

<160> NUMBER OF SEQ ID NOS: 15

<210> SEQ ID NO 1
<211> LENGTH: 300
<212> TYPE: PRT
<213> ORGANISM: Homo sapiens
<220> FEATURE:
<223> OTHER INFORMATION: DcR3

<400> SEQUENCE: 1

Met Arg Ala Leu Glu Gly Pro Gly Leu Ser Leu Leu Cys Leu Val Leu
1               5                   10                  15

Ala Leu Pro Ala Leu Leu Pro Val Pro Ala Val Arg Gly Val Ala Glu

```
                    20                  25                  30
Thr Pro Thr Tyr Pro Trp Arg Asp Ala Glu Thr Gly Glu Arg Leu Val
             35                  40                  45
Cys Ala Gln Cys Pro Pro Gly Thr Phe Val Gln Arg Pro Cys Arg Arg
 50                  55                  60
Asp Ser Pro Thr Thr Cys Gly Pro Cys Pro Pro Arg His Tyr Thr Gln
 65                  70                  75                  80
Phe Trp Asn Tyr Leu Glu Arg Cys Arg Tyr Cys Asn Val Leu Cys Gly
             85                  90                  95
Glu Arg Glu Glu Glu Ala Arg Ala Cys His Ala Thr His Asn Arg Ala
                100                 105                 110
Cys Arg Cys Arg Thr Gly Phe Phe Ala His Ala Gly Phe Cys Leu Glu
            115                 120                 125
His Ala Ser Cys Pro Pro Gly Ala Gly Val Ile Ala Pro Gly Thr Pro
            130                 135                 140
Ser Gln Asn Thr Gln Cys Gln Pro Cys Pro Pro Gly Thr Phe Ser Ala
145                 150                 155                 160
Ser Ser Ser Ser Ser Glu Gln Cys Gln Pro His Arg Asn Cys Thr Ala
                165                 170                 175
Leu Gly Leu Ala Leu Asn Val Pro Gly Ser Ser Ser His Asp Thr Leu
            180                 185                 190
Cys Thr Ser Cys Thr Gly Phe Pro Leu Ser Thr Arg Val Pro Gly Ala
            195                 200                 205
Glu Glu Cys Glu Arg Ala Val Ile Asp Phe Val Ala Phe Gln Asp Ile
            210                 215                 220
Ser Ile Lys Arg Leu Gln Arg Leu Leu Gln Ala Leu Glu Ala Pro Glu
225                 230                 235                 240
Gly Trp Gly Pro Thr Pro Arg Ala Gly Arg Ala Ala Leu Gln Leu Lys
                245                 250                 255
Leu Arg Arg Arg Leu Thr Glu Leu Leu Gly Ala Gln Asp Gly Ala Leu
            260                 265                 270
Leu Val Arg Leu Leu Gln Ala Leu Arg Val Ala Arg Met Pro Gly Leu
            275                 280                 285
Glu Arg Ser Val Arg Glu Arg Phe Leu Pro Val His
            290                 295                 300

<210> SEQ ID NO 2
<211> LENGTH: 227
<212> TYPE: PRT
<213> ORGANISM: Homo sapiens
<220> FEATURE:
<223> OTHER INFORMATION: IgG Fc

<400> SEQUENCE: 2

Asp Lys Thr His Thr Cys Pro Pro Cys Pro Ala Pro Glu Leu Leu Gly
 1                   5                  10                  15
Gly Pro Ser Val Phe Leu Phe Pro Pro Lys Pro Lys Asp Thr Leu Met
             20                  25                  30
Ile Ser Arg Thr Pro Glu Val Thr Cys Val Val Val Asp Val Ser His
             35                  40                  45
Glu Asp Pro Glu Val Lys Phe Asn Trp Tyr Val Asp Gly Val Glu Val
             50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
```

```
                85                  90                  95
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 3
<211> LENGTH: 26
<212> TYPE: DNA
<213> ORGANISM: Artificial Sequence
<220> FEATURE:
<223> OTHER INFORMATION: DcR3 forward primer

<400> SEQUENCE: 3
ggaattcaag gaccatgagg gcgctg                                      26

<210> SEQ ID NO 4
<211> LENGTH: 26
<212> TYPE: DNA
<213> ORGANISM: Artificial Sequence
<220> FEATURE:
<223> OTHER INFORMATION: DcR3 reverse primer

<400> SEQUENCE: 4
ggaattcgtg cacagggagg aagcgc                                      26

<210> SEQ ID NO 5
<211> LENGTH: 20
<212> TYPE: DNA
<213> ORGANISM: Artificial Sequence
<220> FEATURE:
<223> OTHER INFORMATION: IL-4 forward primer

<400> SEQUENCE: 5
cgtcactgac tgtagagagc                                             20

<210> SEQ ID NO 6
<211> LENGTH: 18
<212> TYPE: DNA
<213> ORGANISM: Artificial Sequence
<220> FEATURE:
<223> OTHER INFORMATION: IL-4 reverse primer

<400> SEQUENCE: 6
gggctgtcgt tacatccg                                               18

<210> SEQ ID NO 7
```

```
<211> LENGTH: 20
<212> TYPE: DNA
<213> ORGANISM: Artificial Sequence
<220> FEATURE:
<223> OTHER INFORMATION: IL-10 forward primer

<400> SEQUENCE: 7
gttgccaagc cttgtcagaa                                          20

<210> SEQ ID NO 8
<211> LENGTH: 20
<212> TYPE: DNA
<213> ORGANISM: Artificial Sequence
<220> FEATURE:
<223> OTHER INFORMATION: IL-10 reverse primer

<400> SEQUENCE: 8
tttctgggcc atggttctct                                          20

<210> SEQ ID NO 9
<211> LENGTH: 18
<212> TYPE: DNA
<213> ORGANISM: Artificial Sequence
<220> FEATURE:
<223> OTHER INFORMATION: IL-13 forward primer

<400> SEQUENCE: 9
cttgccttgg tggtcttg                                            18

<210> SEQ ID NO 10
<211> LENGTH: 20
<212> TYPE: DNA
<213> ORGANISM: Artificial Sequence
<220> FEATURE:
<223> OTHER INFORMATION: IL-13 reverse primer

<400> SEQUENCE: 10
tcttctggtc ttgtgtgatg                                          20

<210> SEQ ID NO 11
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 11
aggtggtggt tgtacgctgt g                                        21

<210> SEQ ID NO 12
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 12
tgaacttgcc gtgggtagag                                          20

<210> SEQ ID NO 13
<211> LENGTH: 24
<212> TYPE: DNA
<213> ORGANISM: Artificial Sequence
<220> FEATURE:
<223> OTHER INFORMATION: Arg-I forward primer

<400> SEQUENCE: 13
```
atcataagcc agagactgac tacc                                              24

```
<210> SEQ ID NO 14
<211> LENGTH: 24
<212> TYPE: DNA
<213> ORGANISM: Artificial Sequence
<220> FEATURE:
<223> OTHER INFORMATION: Arg-I reverse primer
```

<400> SEQUENCE: 14
tccagaaagg aactgctaga atac                                              24

```
<210> SEQ ID NO 15
<211> LENGTH: 1620
<212> TYPE: DNA
<213> ORGANISM: Artificial Sequence
<220> FEATURE:
<223> OTHER INFORMATION: DcR3.Fc
```

<400> SEQUENCE: 15

| | |
|---|---|
| atgagggcgc tggaggggcc aggcctgtcg ctgctgtgcc tggtgttggc gctgcctgcc | 60 |
| ctgctgccgg tgccggctgt acgcggagtg gcagaaacac ccacctaccc ctggcgggac | 120 |
| gcagagacag gggagcggct ggtgtgcgcc cagtgccccc aggcaccttt tgtgcagcgg | 180 |
| ccgtgccgcc gagacagccc cacgacgtgt ggccgtgtc accgcgcca ctacacgcag | 240 |
| ttctggaact acctggagcg ctgccgctac tgcaacgtcc tctgcgggga gcgtgaggag | 300 |
| gaggcacggg cttgccacgc cacccacaac cgtgcctgcc gctgccgcac cggcttcttc | 360 |
| gcgcacgctg gtttctgctt ggagcacgca tcgtgtccac ctggtgccgg cgtgattgcc | 420 |
| ccgggcaccc ccagccagaa cacgcagtgc cagccgtgcc ccccaggcac cttctcagcc | 480 |
| agcagctcca gctcagagca gtgccagccc caccgcaact gcacggccct gggcctggcc | 540 |
| ctcaatgtgc aggctcttc ctcccatgac accctgtgca ccagctgcac tggcttcccc | 600 |
| ctcagcacca gggtaccagg agctgaggag tgtgagcgtg ccgtcatcga ctttgtggct | 660 |
| ttccaggaca tctccatcaa gaggctgcag cggctgctgc aggccctcga ggccccggag | 720 |
| ggctggggtc cgacaccaag ggcgggccgc gcggccttgc agctgaagct gcgtcggcgg | 780 |
| ctcacggagc tcctgggggc gcaggacggg gcgctgctgg tgcggctgct gcaggcgctg | 840 |
| cgcgtggcca ggatgcccgg gctggagcgg agcgtccgtg agcgcttcct ccctgtgcac | 900 |
| gaattcgtta cagatctgc agagcccaaa tcttgtgaca aaactcacac atgcccaccg | 960 |
| tgcccagcac ccgaactcct ggggggaccg tcagtcttcc tcttcccccc aaaacccaag | 1020 |
| gacaccctca tgatctcccg gacccctgag gtcacatgcg tggtggtgga cgtgagccac | 1080 |
| gaagaccctg aggtcaagtt caactggtac gtggacggcg tggaggtgca taatgccaag | 1140 |
| acaaagccgc gggaggagca gtacaacagc acgtaccgtg tggtcagcgt cctcaccgtc | 1200 |
| ctgcaccagg actggctgaa tggcaaggag tacaagtgca aggtctccaa caaagccctc | 1260 |
| ccagccccca tcgagaaaac catctccaaa gccaaagggc agccccgaga accacaggtg | 1320 |
| tacaccctgc ccccatcccg ggatgagctg accaagaacc aggtcagcct gacctgcctg | 1380 |
| gtcaaaggct tctatcccag cgacatcgcc gtggagtggg agagcaatgg gcagccggag | 1440 |
| aacaactaca agaccacgcc tcccgtgctg gactccgacg gctccttctt cctctacagc | 1500 |
| aagctcaccg tggacaagag caggtggcag caggggaacg tcttctcatg ctccgtgatg | 1560 |
| catgaggctc tgcacaacca ctacacgcag aagagcctct ccctgtctcc gggtaaatag | 1620 |

RECOMBINANT DECOY RECEPTOR 3 FOR TREATING SPINAL CORD INJURY

BACKGROUND OF THE INVENTION

1. Field of the Invention

The present disclosure relates to methods for treating spinal cord injury.

2. Description of Related Art

Spinal cord injury (SCI) refers to damage to the spinal cord resulting from trauma (e.g. a car crash) or from disease (e.g. cancer) or degeneration. According to WHO statistics, as many as 500,000 people suffer a spinal cord injury every year, with road traffic crashes, falls and violence as the three leading causes.

SCI causes loss of neurons and axons resulting in motor and sensory function impairments. For adult mammals, SCI may cause incurable neurological dysfunction due to failure of axonal regeneration. Symptoms of SCI depend on the severity of injury and its location on the spinal cord; common symptoms include partial or complete loss of sensory function or motor control of arms, legs, and/or body, while the most severe SCI may affect the autonomic systems that regulate breathing, bowel and bladder control, heart rate, and blood pressure. Most people with SCI experience chronic pain, and an estimated 20-30% of SCI patients exhibit clinically signs of depression, which in turn has a negative impact on improvements in functioning and overall health of the patient. Also, SCI may render a person dependent on caregivers. Accordingly, spinal cord injury may result in devastating psychological and psychological damage to the affected individuals and cause an enormous financial cost to the patients and/or their families.

The pathophysiological processes that underlie SCI comprise multiple phases of injury. Initial physical trauma to the spinal cord contains traction injury, compression forces, and direct mechanical disruption of neural elements. Microvascular injuries with hemorrhage and disruption of blood-spinal cord barrier are followed by edema, ischemia, release of cytotoxic chemicals from inflammatory pathways, and electrolyte shifts. Subsequently, the secondary injury cascade is ignited that compounds the initial mechanical injury with cell necrosis and apoptosis to endanger surviving neurons in the neighborhood. Progression from the acute to the chronic phase results in secondary neurodegenerative events, such as demyelination, Wallerian degeneration, and axonal dieback, while a non-permissive tissue environment is established largely because of astroglial scar formation, thus contributing to irreversible loss of function. The inflammatory response plays a critical role in the secondary phase after SCI through modulation of a series of complex cellular and molecular interactions, which further reduce the chance of recovery of penumbra neurons and render functional recovery almost hopeless.

In spite of decades of research and development, the cure for severe SCI remains elusive and current treatment is limited to early administration of high dose steroids and acute surgical intervention to minimize cord edema and the following cascades of injuries. Accordingly, there exists a need in the art for providing for treating spinal cord injury or to improve the locomotor function recovery of a spinal cord injured subject.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

One purpose of the present disclosure is to provide method for treating spinal cord injuries; in particular, to improve the locomotor function recovery of individuals with spinal cord injuries. Accordingly, in one aspect, the present disclosure is directed to a method for treating spinal cord injury in a subject in need thereof, and in another aspect, the present disclosure is directed to a method for improving the locomotor function recovery of a spinal cord injured subject.

According to embodiments of the present disclosure, the methods according to the above-mentioned aspects comprise the step of administering to the subject an effective amount of recombinant decoy receptor 3 (DcR3) polypeptide.

According to certain optional embodiments of the present disclosure, the recombinant DcR3 polypeptide comprises a human DcR3 polypeptide or a fragment thereof and an immunoglobulin constant region fragment (Fc region) or a fragment thereof.

In certain optional embodiments, the present human DcR3 polypeptide or the fragment thereof has a sequence that has at least 80, 90 or 95, or 100 percent amino acid sequence identity to SEQ ID No. 1.

According to some optional embodiments of the present disclosure, the Fc region or the fragment thereof comprises human immunoglobulin G (IgG) Fc region or a fragment thereof.

In various optional embodiments, the present the IgG Fc region or the fragment thereof comprises a sequence that has at least 80, 90 or 95, or 100 percent amino acid sequence identity to SEQ ID No. 2.

According to some optional embodiments of the present disclosure, the human DcR3 polypeptide or the fragment thereof comprises a sequence having at least 80, 90 or 95, or 100 percent amino acid sequence identity to SEQ ID No. 1, and the Fc region or the fragment thereof comprises a sequence having at least 80, 90 or 95, or 100 percent amino acid sequence identity to SEQ ID No. 2.

According to certain optional embodiments of the present disclosure, the subject is a rat, and the effective amount is 1 μg/kg body weight to 1 mg/kg body weight; preferably, 10 μg/kg body weight to 500 μg/kg body weight; more preferably, 50 μg/kg body weight to 100 μg/kg body weight.

According to some other embodiments of the present disclosure, the subject is a human, and the effective amount is 0.15 μg/kg body weight to 250 μg/kg body weight; preferably, 1 μg/kg body weight to 100 μg/kg body weight; and more preferably, 5 μg/kg body weight to 50 μg/kg body weight.

According to embodiments of the present disclosure, the recombinant DcR3 polypeptide is administered via injection, such as intraspinal injection.

In another aspect, the present disclosure is directed to the use of recombinant DcR3 polypeptide in the manufacture of a pharmaceutical composition for treating spinal cord injury in a subject in need thereof.

In yet another aspect, the present disclosure is directed to the use of recombinant DcR3 polypeptide in the manufacture of a pharmaceutical composition for improving the locomotor function recovery of a spinal cord injured subject.

In still another aspect, the present disclosure is directed to a recombinant DcR3 polypeptide for use in the treatment of spinal cord injury.

In yet another aspect, the present disclosure is directed to a recombinant DcR3 polypeptide for use in improving the locomotor function recovery of a spinal cord injured subject.

As could be appreciated, above-mentioned embodiments of recombinant DCR3 polypeptides are also applicable in these aspects.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DETAILED DESCRIPTION OF THE INVENTION

Figure 1:
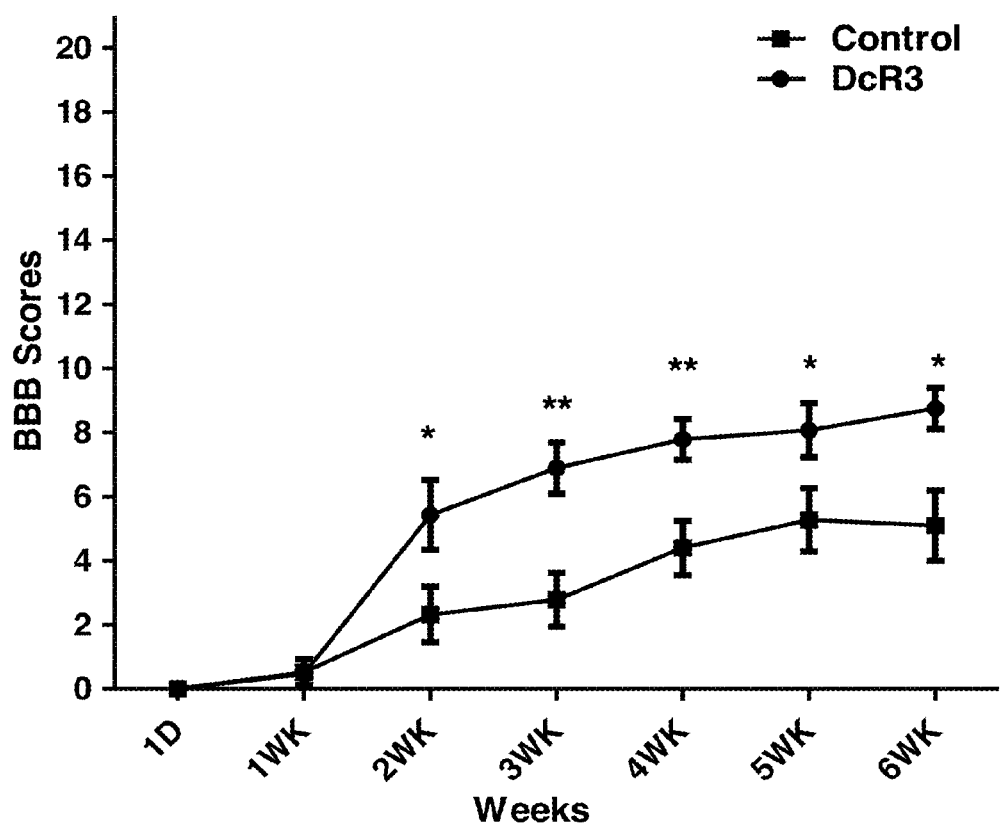
FIG. 1 is a line graph demonstrating the efficacy of the present DcR3 treatment in improving hindlimb functional recovery of SCI rats; $*P<0.05$, $**P<0.01$.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used herein, the term "polypeptide" denotes a polymer of amino acid residues. According to embodiments of the present disclosure, the polypeptide may be synthetic, meaning that it may be produced by human intervention using techniques such as, chemical synthesis, recombinant genetic techniques, or fragmentation of the whole protein or the like. Throughout the present disclosure, the positions of any specified amino acid residues within a polypeptide are numbered starting from the N terminus of the polypeptide.

Throughout the present disclosure, the term "fragment thereof" refers to a fragment of the molecule identified having the same activity with respect to the specific functionality identified for the full length molecule.

"Percentage (%) amino acid sequence identity" with respect to the synthetic polypeptide sequences identified herein is defined as the percentage of amino acid residues in a candidate sequence that are identical with the amino acid residues in the specific polypeptide sequence, after aligning the sequences and introducing gaps, if necessary, to achieve the maximum percent amino acid sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given polypeptide A to a given polypeptide B (which can alternatively be phrased as a given polypeptide A that has a certain % amino acid sequence identity to a given polypeptide B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "conservative variation" as used herein denotes the replacement of an amino acid residue by another, biologically similar residue. Examples of conservative variations include the substitution of one hydrophobic residue such as isoleucine, valine, leucine, or methionine for one another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The terms "treatment" and "treating" are used herein to include curative or palliative treatment that results in a desired pharmaceutical and/or physiological effect. Preferably, the effect is therapeutic in terms of curing the spinal cord injury (SCI), partially or completely. In particular, the term "treating" relates to the application or administration of the physical and/or chemical intervention to a subject, who has a medical condition associated with the SCI, a symptom of the condition, or a disease or disorder secondary to the condition, with the purpose to partially or completely alleviate, ameliorate, relieve, delay onset of, inhibit progression of, reduce severity of, and/or reduce incidence of one or more symptoms or features of the SCI and/or condition associated therewith. Treatment may be administered to a subject who does not exhibit signs of the SCI and/or condition associated therewith and/or to a subject who exhibits only early signs of the SCI and/or condition associated therewith for the purpose of decreasing the risk of developing pathology associated with the SCI and/or condition associated therewith. Treatment is generally "effective" if one or more symptoms or clinical markers are reduced as that term is defined herein.

As used herein, the term "improve" shall have its plain and ordinary meaning to one skilled in the art of pharmaceutical or medical sciences. Also, the term "improve the locomotor function recovery" means that the present DcR3 polypeptide or a composition comprising the same is administered to or a method is used for a subject suffered from SCI for a period effective to improve the locomotor function(s) of the subject, as determined by comparison with locomotor function(s) in subjects not being administered the present DcR3 polypeptide or a composition comprising the same or using the method.

The term "effective amount" as used herein refers to the quantity of a component which is sufficient to yield a desired response. The specific effective amount will vary with such factors as the particular condition being treated, the physical condition of the subject (e.g., the subject's body mass, age, or gender), the type of mammal or animal being treated, the duration of the treatment, the nature of concurrent therapy (if any), and the specific formulations employed. An effective amount is also one in which any toxic or detrimental effects of the compound or composition are outweighed by the therapeutically beneficial effects.

As used herein, the terms "dose," "dose unit," and/or "dosage unit" refer to a portion of a pharmaceutical composition that contains an amount of a therapeutic agent suitable for a single administration to provide a therapeutic effect. Such dosage units may be administered continuously, one to a small plurality (e.g., 1 to about 4) of times per day, or as many times as needed to elicit a desired therapeutic response. A particular dosage form can be selected to accommodate any desired frequency of administration to achieve a specified daily dose.

The terms "application" or "administration" are used interchangeably herein to refer means providing a recombinant DcR3 polypeptide according to embodiments of the present disclosure or a pharmaceutical composition comprising the same to a subject to treat SCI or to improve the locomotor function recovery in the subject.

The term "excipient" as used herein means any inert substance (such as a powder or liquid) that forms a vehicle/carrier for the DcR3 polypeptide(s) of the present disclosure. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

As used herein, a "pharmaceutically acceptable" component is one that is suitable for use with humans and/or animals without undue adverse side effects (such as toxicity, irritation, and allergic response) commensurate with a reasonable benefit/risk ratio. Also, each excipient must be "acceptable" in the sense of being compatible with the other ingredients of the pharmaceutical formulation. The carrier can be in the form of a solid, semi-solid, or liquid diluent, cream or a capsule.

The term "subject" refers to a mammal including the human species that is treatable with the present DcR3 polypeptides, compositions comprising the same, and/or methods of the present invention. The term "subject" is intended to refer to both the male and female gender unless one gender is specifically indicated.

Decoy receptor 3 (DcR3) is a soluble member of tumor necrosis factor receptor superfamily (TNFRSF). Its function as a decoy receptor to neutralize cytokine ligands of TNFSF members (including Fas ligand (FasL/TNFSF6/CD95L), LIGHT (TNFSF14), and TNF-like molecule 1A (TL1A/TNFSF15)) leads to the inhibition of the bioactivities of these ligands. Prior studies have demonstrated the DcR3-induced suppression of T-cell activity in response to alloantigens through the LIGHT-HVEM pathway and of apoptosis in cancer cells through the LIGHT and TL1A pathways. FasL and LIGHT are involved in apoptotic and inflammatory mechanisms and TL1A is found to promote a T-cell response to IL-2. Furthermore, DcR3 has been demonstrated to antagonize TL1A effects, leading to endothelial cell migration, proliferation differentiation, MMP-2 activation and angiogenesis. Therefore, DcR3 molecule can function as an immunomodulatory with regards to blocking the biological functions of its ligands, leading to attenuation of T-cell activation, anti-apoptosis, anti-inflammation, promoted endothelial cell activities (migration, proliferation, and differentiation), and angiogenesis. In addition, DcR3 had been characterized with regulatory function in M2 macrophage differentiation. However, DcR3 have not been evaluated in the central nerve system, specifically in the spinal cord injury, before the present invention.

The present disclosure is based, at least, on the finding that recombinant DcR3 polypeptide may promote the healing of spinal cord injuries via a variety of mechanisms. Examples of the present disclosure demonstrate that the present recombinant DcR3 polypeptides may improve hindlimb functional recovery of SCI subjects and reduce the sizes of wound cavities. Also, the present recombinant DcR3 treatment may increase the expressions of anti-inflammatory cytokines, such IL-4 and IL-10, and recruit more M2 macrophages at the lesion sites. The present recombinant DcR3 polypeptide is also found to promote angiogenesis at lesion sites. Accordingly, the present recombinant DcR3 polypeptides are useful for treating spinal cord injuries and/or improving the locomotor function recovery of a spinal cord injured subject.

Thus, in one aspect, the present disclosure is directed to a method for treating spinal cord injuries in a subject in need thereof. According to certain embodiments, the method comprises the step of administering to the subject an effective amount of recombinant DcR3 polypeptide.

For example, the recombinant DcR3 polypeptide according to optional embodiments of the present disclosure may comprise a human DcR3 polypeptide or a fragment thereof and an immunoglobulin constant region fragment (Fc region) or a fragment thereof.

In various embodiments of the present disclosure, the human DcR3 polypeptide or the fragment thereof has a sequence that has at least 80 percent amino acid sequence identity to SEQ ID No. 1 (NCBI Reference Sequence: NP_003814.1). For example, the amino acid sequence identity may be 80, 81, 82, 83, 84, 85, 86, 87, 88, 89, 90, 91, 92, 93, 94, 95, 96, 97, 98, 99, 100%. As could be appreciated by persons having ordinary skill in the art, the variation in the amino acid sequence identity may arise from conservative variation; however, the present invention is not limited thereto.

According to some optional embodiments of the present disclosure, the Fc region or the fragment thereof comprises human immunoglobulin G (IgG) Fc region or a fragment thereof. One illustrative example of the human IgG Fc region has the amino acid sequence set forth in SEQ ID No. 2. According to embodiments of the present disclosure, the human IgG Fc region or the fragment thereof has at least 80 percent amino acid sequence identity to SEQ ID No. 2. For example, the amino acid sequence identity may be 80, 81, 82, 83, 84, 85, 86, 87, 88, 89, 90, 91, 92, 93, 94, 95, 96, 97, 98, 99, 100%. As could be appreciated by persons having ordinary skill in the art, the variation in the amino acid sequence identity may arise from conservative variation; however, the present invention is not limited thereto.

In some optional embodiments, the human DcR3 polypeptide or the fragment thereof and the Fc region or the fragment thereof respectively comprise a sequence having at least 80 percent amino acid sequence identity to SEQ ID Nos. 1 and 2.

According to embodiments of the present disclosure, the subject receiving the present recombinant DcR3 treatment is a rat, and the effective amount for treating the SCI and/or improving the locomotor function recovery is about 1 µg/kg body weight to 1 mg/kg body weight. For example, the effective amount can be 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 1000 µg/kg body weight.

In the case where the subject is a human, the effective amount is 0.15 µg/kg body weight to 250 µg/kg body weight. For example, the effective amount can be 0.15, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 1000 µg/kg body weight. As could appreciated, human equivalent dose (HEQ) for the present recombinant DcR3 polypeptide or pharmaceutical composition comprising the same can be calculated by persons having ordinary skill in the art based on the animal doses provided in the working examples below. In particular, one may follow the guidance for industry published by US Food and Drug Administration (FDA) entitled "Estimating the Maximum Safe Starting Dose in Initial Clinical Trials for Therapeutics in Adult Healthy Volunteers (July 2005)" in estimating a maximum safe dosage for use in human subjects. For example, the above-mentioned range of the effective amount for human subject is derived from the effective dosages for rats using the conversion factors provided in Table 2 of said FDA guidance.

For example, in some working examples, therapeutic effects were observed in rats (225 to 250 grams) treated with 15 µg recombinant DcR3 polypeptide, thereby giving an effective amount of about 60-67 µg/body weight. Based on the dose of rats, the HED for a human weighing between 50 to 80 kilograms is in the range of 9.72-10.854 µg/body weight. Therefore, according to certain embodiments of the present According to embodiments of the present disclosure, the recombinant DcR3 polypeptide is administered via injection, such as intraspinal injection.

For the purpose of administration, the recombinant DcR3 polypeptide may be formulated into pharmaceutical compositions for use in the methods described above, which falls within other aspects of the present disclosure.

According to one embodiment of the present disclosure, the pharmaceutical composition comprises a recombinant DcR3 polypeptide according to any of the above-mentioned embodiments, and the recombinant DcR3 polypeptide is present in an effective amount sufficient to treat SCI in the subject and/or improve the locomotor function of the subject. The pharmaceutical composition also comprises a pharmaceutically acceptable excipient for the recombinant DcR3 polypeptide.

According to optional embodiments of the present disclosure, the recombinant DcR3 polypeptide is present in the pharmaceutical composition in an amount of about 0.01-1, 000 μg/μl; preferably, about 0.1-500 μg/μl; and more preferably, about 1-250 μg/μl. For example, the concentration of the synthetic peptides may be about 0.01, 0.05, 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, or 1,000 μg/μl.

The pharmaceutical composition is prepared in accordance with acceptable pharmaceutical procedures, such as described in Remington's The Science and Practice of Pharmacy, 22$^{nd}$ edition, ed. Allen, Loyd V., Jr, Pharmaceutical Press, Pa (2012).

The choice of a pharmaceutically acceptable excipient to be used in conjunction with the present recombinant DcR3 polypeptide is basically determined by the way the pharmaceutical composition is to be administered. According to one optional embodiment of the present disclosure, the pharmaceutical composition may be administered locally via intraspinal injection. In this case, the recombinant DcR3 polypeptide may be formulated with a pharmaceutically acceptable excipient such as a sterile aqueous solution, which is preferably isotonic with the body fluid of the recipient. Such formulations may be prepared by dissolving or suspending the solid active ingredient in water containing physiologically compatible substances (such as sodium chloride, glycine, and the like) and having a buffered pH compatible with physiological conditions to produce an aqueous solution, and then rendering said solution sterile. Other diluents or solvent suitable for manufacturing sterile injectable solution or suspension include, but are not limited to, 1,3-butanediol, mannitol, water, and Ringer's solution. Fatty acids, such as oleic acid and its glyceride derivatives are also useful for preparing the injectable, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

According to optional embodiment of the present invention, the pharmaceutical composition may further comprise pharmaceutical agents for treating spinal cord injuries. As could be appreciated, providing additional pharmaceutical agents to the lesion may facilitate the treatment of SCI.

Still optionally, pharmaceutical compositions of the present invention can also comprise various pharmaceutically-acceptable additives well known to the art. Said additives include, but are not limited to, drying agent, anti-itch agents, anti-foaming agents, buffers, neutralizing agents, pH adjusting agents, coloring agents, discoloring agents, emollients, emulsifying agents, emulsion stabilizers, viscosity builders, humectants, odorants, preservatives, antioxidants, chemical stabilizers, thickening agents, stiffening agents, or suspending agents.

Also encompassed in the scope of the claimed invention are use of a recombinant DcR3 polypeptide for treating spinal cord injuries in a subject in need thereof and/or use of a recombinant DcR3 polypeptide for improving the locomotor function recovery of a spinal cord injured subject.

In certain embodiments, recombinant DcR3 polypeptides suitable for such uses are those discussed-above in connection with other aspects/embodiments of the present disclosure.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

Example 1

DcR3.Fc Treatment Improved Hindlimb Function after Spinal Cord Injury

To investigate the efficacy of recombinant human DcR3 polypeptide on hindlimb activities, recombinant human DcR3 polypeptide (hereinafter, the DcR3.Fc protein) was first prepared and then administered to rats with spinal cord injuries.

First, the open reading frame of the human DcR3 gene was isolated by RT-PCR using the forward primer of SEQ ID No. 3 and reverse primer of SEQ ID No. 4. The amplified product was ligated in-frame into the EcoRI-cut pUC19-IgG1-Fc vector containing the cDNA of the human IgG1 Fc. The fusion gene was then subcloned into the pBacPAK9 vector (Clontech Laboratories, Palo Alto, Calif.) and cotransfected with linearized BacPAK6 DNA (Clontech Laboratories) into Sf21 cells. The supernatant from recombinant virus-infected Sf21 cells was filtered and purified on protein A-Sepharose beads. The bound DcR3.Fc protein was then eluted with 0.1 M glycine buffer (pH 3.0) followed by dialysis against PBS.

Sprague Dawley (SD) rats were obtained from Laboratory Animal Center of Yang Ming University (Taipei, Taiwan). Adult female SD rats ranging from 225-250 g were used for the induction of SCI. Animal handling and experimental protocols were reviewed and approved by the Animals Committee of Taipei Veterans General Hospital (Taipei, Taiwan) and Institutional Animal Care and Use Committees of National Yang-Ming University (Taipei, Taiwan), and were performed in compliance with national animal welfare regulations.

Spinal cord injury was induced using the protocol as follows. Rats were anaesthetized and then underwent a T8-10 laminectomy. A 10-g weight steel rod was allowed to drop 5 cm onto the exposed dura at the T9 vertebral level to produce a contusion injury.

Two experimental animal groups were used in this example. Rats in the DcR3 group (n=7) were contused rats received intraspinal injection of DcR3.Fc protein (15 μg in 5 μl of normal saline) using a 5-μl Hamilton syringe fitted with a 33-gauge needle. The needle was held in place for 5 minutes after the injection, before it was slowly withdrawn from the spinal cord. In control group (n=10), contused rats was injected with 5 μl of normal saline using the same protocol described above. Manual emptying of the bladders was performed twice daily.

All animals received behavioral testing 1 day and every week post-surgery until termination. All behavioral tests were performed videotaped and both of the two examiners were blind to each group when they participated in the behavioral evaluation. The hindlimb locomotor behavior of rats was evaluated by the Basso, Beattie, Bresnahan (BBB) open field locomotion test, in which the hindlimb movement was scored from 0 (no observable hindlimb movement) to 21 (normal hind movement) points. Results were expressed as the mean±standard error of the mean (SEM). Statistical comparisons in this and the following examples were performed by two-tailed Student's t test was used for using GraphPad Prism® software. *P<0.05 was considered significant, unless otherwise specified.

The results of the BBB test are summarized in FIG. 1. The data in FIG. 1 indicated that, during the first week post-injury, no significant differences in the hindlimb activities between the DcR3 group and the control group were found. However, starting from week 2, SCI rats with the present DcR3.Fc treatment exhibited higher BBB scores than the control rats did (5.4 compared with 2.3). The significance remained until the end of 6-week observation (8.8 compared with 5.1), indicating a better hind limb functional recovery of hindlimb activities with the present DcR3.Fc treatment. These results suggest that DcR3.Fc treatment may improve the functional regeneration after SCI.

Example 2

DcR3.Fc Treatment Resulted in Smaller Wound Cavities and Increased Myelin Sparing at Lesion Sites At 6 weeks post-injury, rats from example 1, above, were sacrificed to evaluate the wound cavities of the rats.

Animals (n=4 per group) were anaesthetized using a sodium pentobarbital and were perfused intravascularly with 0.9% saline and 4% paraformaldehyde in PBS at 6 weeks post-injury. Samples of spinal cords at the lesion sites (1 cm in length) were removed from the experimental animals, post-fixed overnight in 4% PFA, rinsed, cryoprotected in graded sucrose, and embedded into the optimal cutting temperature compound at −20° C. Spinal cord was transversely sectioned (20 µm thick) and then placed on slides. Cavity size was quantified using the protocol as follows. Briefly, hematoxylin and eosin (H&E) was used to stain nuclei and eosin for cavities and Luxol fast blue (LFB) used to identify myelinated white matter. Images were photographed from the rostral end to the caudal end throughout the injury site at ×2.5 magnification with a microscope camera (20 sections per animal, 200 µm between sections). For quantification, the images of H&E staining were converted to gray scale (0-255 levels such that 0=black pixel, 255=white pixel), and the total cord area (0-255) and the optimized threshold values of brightness (≥225) as cavity area in each section were determined by using the ImageJ 1.44d software (Wayne Rasband, National Institutes of Health, Bethesda, Md., USA). The cavity area was calculated as a percentage of total cord area for each section, and the section with the highest cavity area was assumed to be the central position of the injury. The LFB-positive area was measured as the myelinated area. After the myelinated area in each section was determined, the Cavalieri method was used to calculate the total volume by summing their individual subvolumes. Individual subvolumes were calculated by multiplying the myelinated area (A)×D, where D represents the distance between sections (200 µm).

Figure 2A:
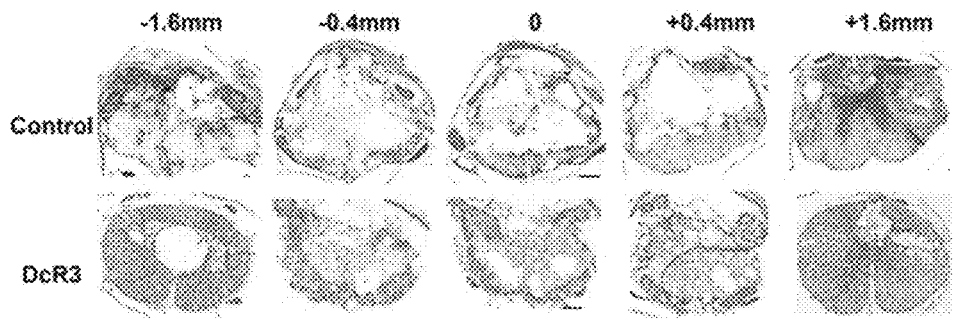
FIG. 2A provides representative photographs indicating that the present DcR3 treatment results in a smaller wound cavity at the lesion site.
Figure 2B:
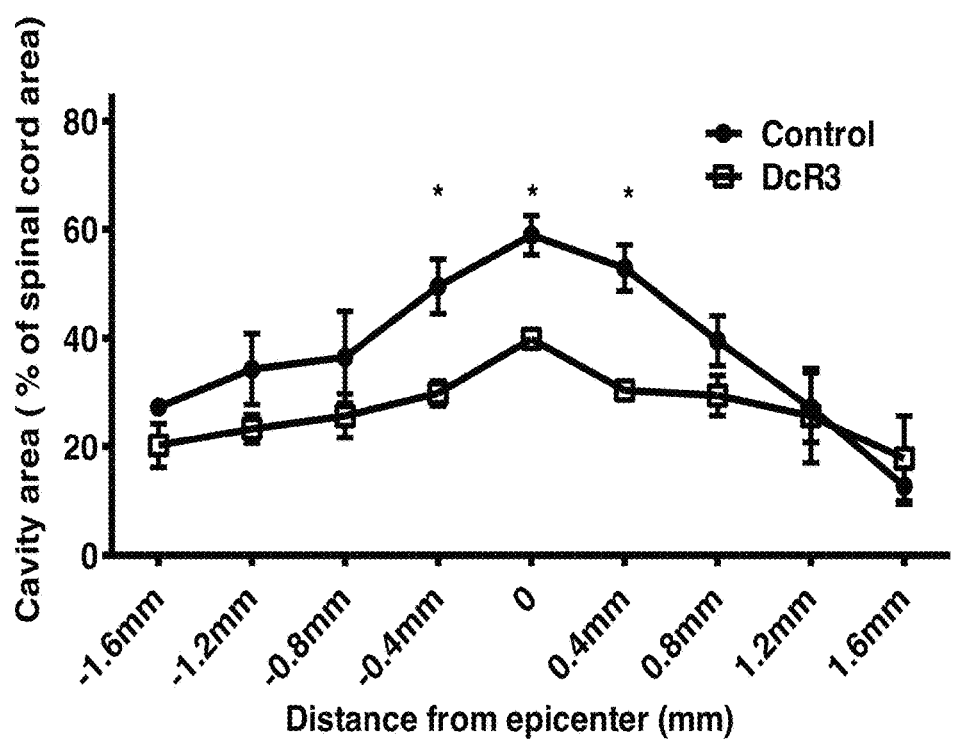
FIG. 2B is a line graph providing quantitative data regarding the cavity area and distance between the wound cavity and the lesion center; $*P<0.05$.

The representative photographs provided in FIG. 2A, as well as the quantitative data in FIG. 2B indicated that SCI rats with DcR3.Fc treatment, as compared with the control group, had smaller wound cavities close to the lesion centers, and the differences were of statistical significance at the epicenter (39% vs. 59%), as well as rostral (−0.4 mm; 29% vs. 49%) to caudal (0.4 mm; 30% vs. 58%). These results suggested that the present DcR3.Fc treatment reduced the degree of damage caused by neuro-inflammation after SCI.

Figure 2C:
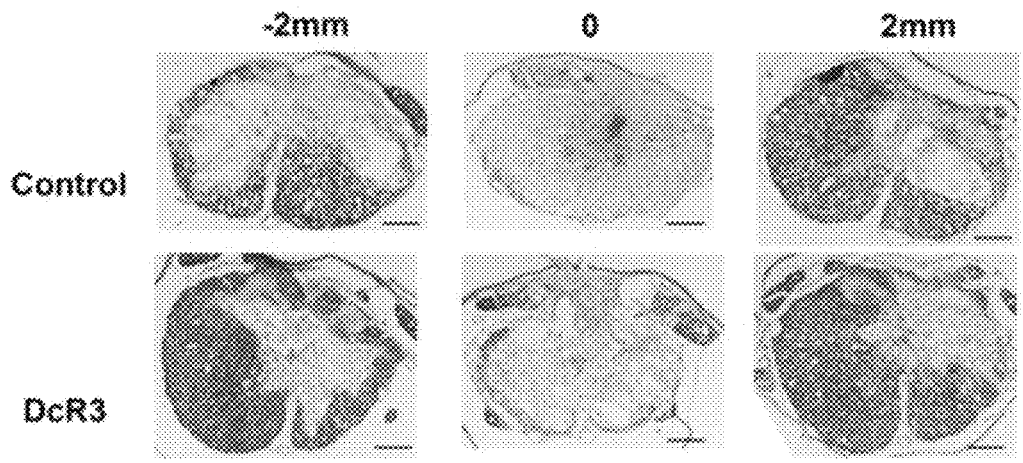
FIG. 2C is a representative photograph showing the LFB staining of the transverse spinal cord sections (−2, 0, and 2 mm) in DcR3.Fc-treated and control SCI rats (scale bar: 250 μm)
Figure 2D:
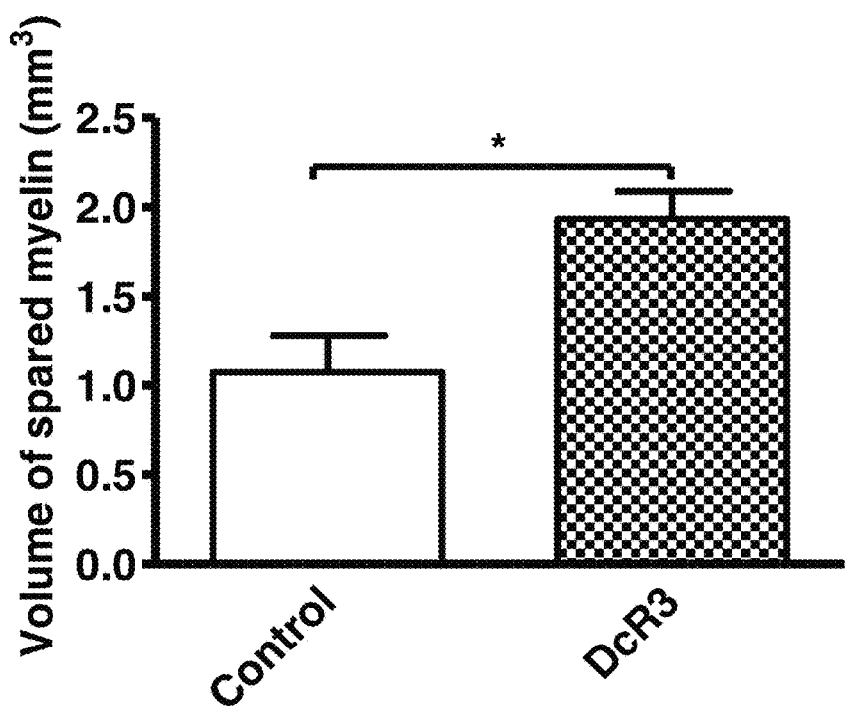
FIG. 2D is a bar graph illustrating the quantified volumes of myelin sparing from −2 mm rostral to 2 mm caudal of the epicenter at the lesion site; $*P<0.05$.

Further, the data in FIG. 2C and FIG. 2D demonstrated, collectively, that the DcR3.Fc-treated rats had higher tissue volume than the control group. Specifically, a higher volume of white matter sparing with more intact structure was observed in DcR3.Fc-treated rats than that of control group (1.934 vs. 1.075 mm$^3$).

Together, the results in this Example suggested that the present DcR3.Fc treatment can significantly reduce tissue damage at the lesion site after SCI.

Example 3

DcR3 Treatment Reduced LPS-Induced NO Production and iNOS Expression in Microglia Primary Culture Primary mixed-glia culture was prepared from spinal cord of 250 g adult Sprague-Dawley rats. Briefly, the spinal cord was removed from the skulls, the meninges and blood vessels were excised carefully, and the spinal cord was chopped finely with scissors. The cell aggregations were further dissociated using 0.25% trypsin and 0.05% EDTA by gentle trituration using a pipette, followed by washing in DMEM containing 10% fetal bovine serum (FBS) and centrifugation. The pellet was resuspended in Dulbecco's Modified Eagle's medium (DMEM), passed through a 70-micron nylon mesh, followed by a second wash and centrifugation. Thereafter, cells were seeded in a density of $5 \times 10^5$ cells/ml and incubated at 37° C. with 5% $CO_2$ for 48 hours. After the incubation, any non-adherent cells were removed and fresh DMEM was added. For microglia enrichment, cultures were thoroughly mixed using an orbital shaker (120 rpm at room temperature) for 2 hours. Then, cells suspended in the culture medium were collected and centrifuged at 1500 rpm for 15 minutes at 4° C. The cells pellet was resuspended and diluted with fresh DMEM to a final concentration of $5 \times 10^5$ cells/mL, and the cell suspension was added to each well of a 48-well plate. 20 minutes later, any non-adherent cells were discarded and adherent cells were maintained in fresh DMEM. The enriched microglia were >85% pure as determined by counting the OX42-positive cells and total cells stained with 4',6'-diamidino-2-phenylindole (DAPI, Sigma-Aldrich).

For lipopolysaccharides (LPS) stimulation, microglia cells were pre-sensitized with 1 µg/ml LPS in serum-free DMEM for 24 hours. After LPS stimulation, the medium was replaced with DMEM with 100 ng/ml DcR3.FC (DcR3.Fc/LPS group) or DMEM only (LPS group) for 24 hours. Then, the culture medium was collected for nitric oxide (NO) assay, and microglia cells were fixed by 4% paraformaldehyde for immunohistochemistry. Nitric oxide production was assessed using the Griess reaction. Briefly, the culture medium was mixed with Griess reagents (1% sulfa-nilaminde, 0.1% naphthylethylene diamine dihydrochloride, and 2% phosphoric acid) and incubated at room temperature for 10 minutes. The absorbance of the resultant products was measured at 540 nm. Sodium nitrite ($NaNO_2$) was used as a standard to calculate nitrogen dioxide concentrations.

Figure 3A:
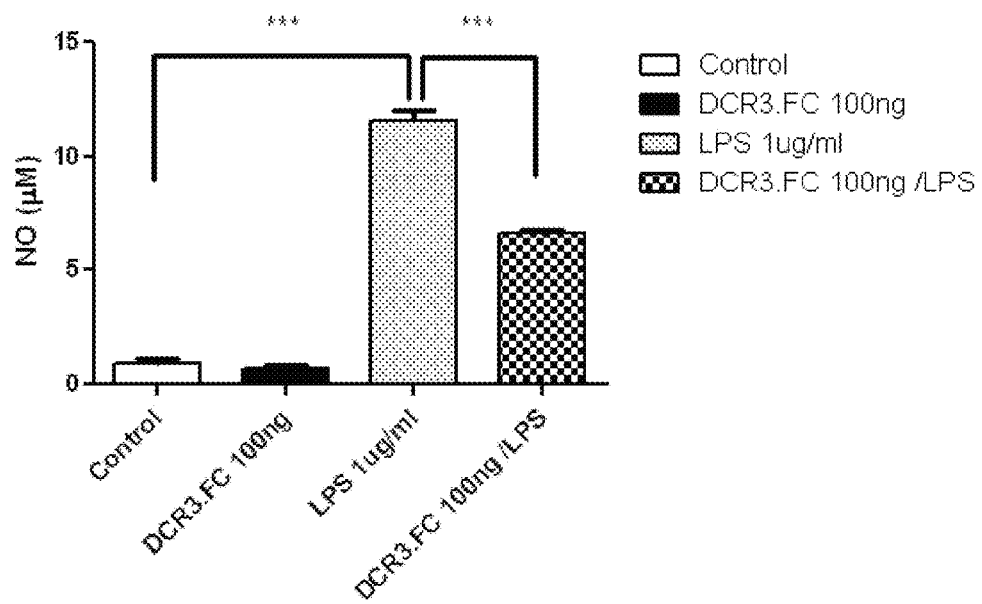
FIG. 3A is a bar graph demonstrating that the present DcR3 treatment reduces LPS-induced NO production; $***P<0.001$.

The results of NO assay are summarized in FIG. 3A, which indicated that NO production was elevated in microglial cells after LPS-stimulation (LPS group), and the present DcR3 treatment significantly reduced the LPS-induced the NO production (DcR3.Fc/LPS group) (***p<0.001, n=3).

Figure 3B:
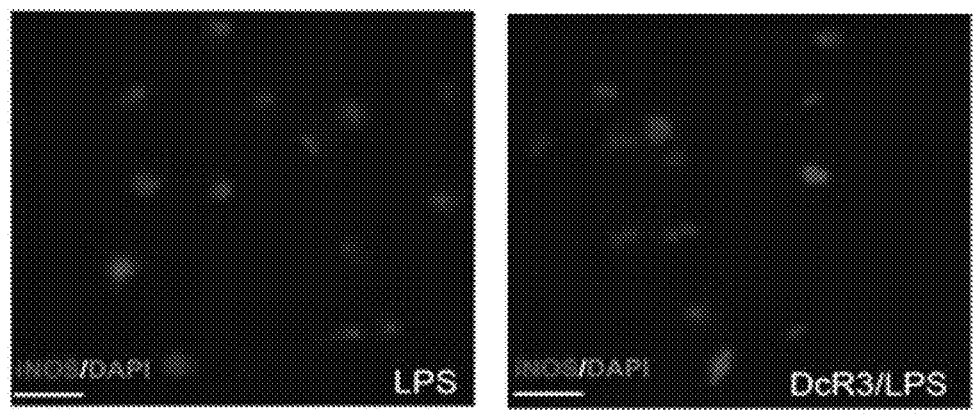
FIG. 3B provides photographs indicating that the present DcR3 treatment reduces iNOS expression on LPS-induced microglia.
Figure 3C:
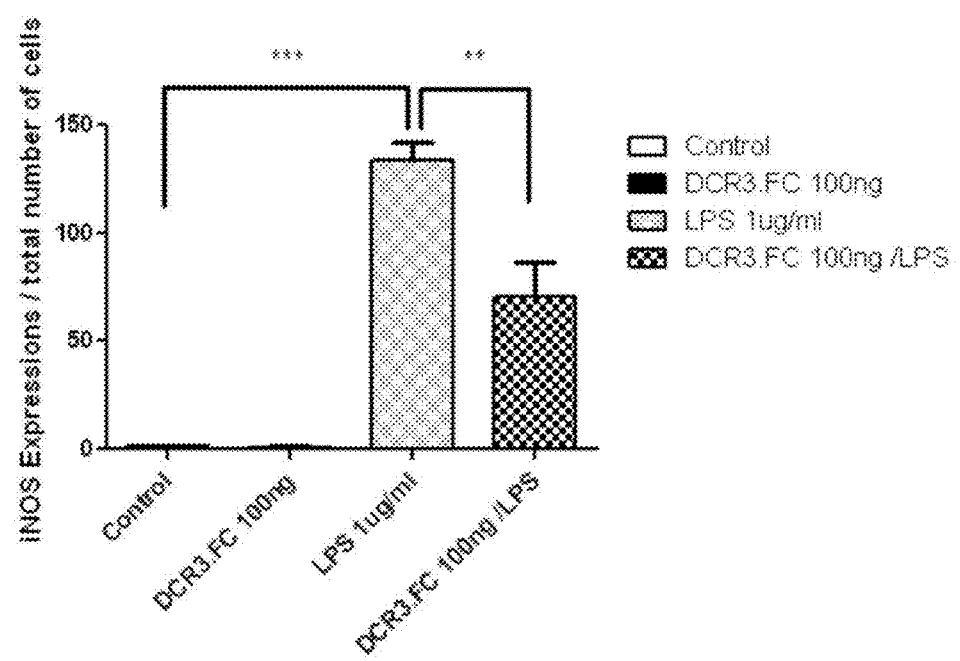
FIG. 3C is a bar graph providing quantitative data regarding the iNOS expression; $P<0.001$, $*P<0.001$.

The photographs in FIG. 3B indicated that DcR3 treatment reduced iNOS expression on LPS-stimulated microglia. Also, the bar graph in FIG. 3C demonstrated that LPS stimulation significantly increased iNOS mRNA expression in microglia cells (LPS group vs. Control group), while the administration of DcR3.Fc reduced the LPS-induced iNOS mRNA expression (DcR3.Fc/LPS group vs. LPS group) (n=3 in each group; p<0.01, *p<0.001).

Example 4

DcR3 Treatment Increased the Expressions of Anti-Inflammatory Cytokines

As could be appreciated, spinal cord injury induces neuroinflammation, which results in devastating neuronal death. Results from Examples 1 to 3 clearly established that the present DcR3.Fc can promote better functional recovery (Example 1), minimize wound cavities and increase myelin sparing (Example 2) of SCI rats, and reduce nitric oxide (NO) production and iNOS expression from microglia induced by lipopolysaccharide (LPS) in vitro (Example 3) and ex vivo (data not provided). In this example, the mRNA expressions of cytokines at 7 days post-injury were analyzed.

At 7-day post-injury, 5-mm spinal cord tissues from lesion site were preserved using Allprotect™ Tissue Reagent (QIAGEN®, Darmstadt, Germany) and homogenized with the MagNA Lyser Instrument (Roche®, Penzberg, Germany). Total RNA was extracted using AllPrep® DNA/RNA/Protein Mini Kit (QIAGEN®, Darmstadt, Germany) per the manufacture's instruction. Expression levels of interleukin-4 (IL-4), IL-10 and IL-13 mRNA were determined by quantitative PCR (qPCR) using glyceraldehyde 3-phosphate dehydrogenase (GAPDH) as an internal control for normalization. Specifically, cDNA synthesis was primed with oligo dT and then reverse-transcribed using Reverse Transcriptase kit (QIAGEN®); cDNA levels were quantified using primer pairs (SEQ ID Nos. 5-12) and a FastStart Universal SYBR Green Master (Roche) on a StepOne™ (Applied Biosystems). All qPCR assays were performed in triplicate, and the specificity of the reaction was determined by melting curve analysis; both positive and negative controls were included on the same plate for qPCR. Total RNA was extracted using TRIzol reagent (Invitrogen™) according to the manufacturer's instructions. First-strand cDNA was synthesized using a RevertAid First-Strand cDNA Synthesis Kit (Thermo Scientific) as per the manufacturer's instructions. The PCR reaction was performed in a LightCycler® System SW 3.5.3 (Roche Applied Science) under the following conditions: PCR mixtures were denatured at 95° C. for 5 minutes, followed by 45 cycles of 15 seconds at 95° C., 30 seconds at 60° C., and 30 seconds at 72° C. for amplification. The mRNA expression level of each target gene was normalized to the respective 18S rRNA expression. The relative differences in expressions between groups were analyzed on the basis of cycle time values using the comparative threshold cycle (Ct) method, in which Ct is the cycle exhibiting the first detectable increase in SYBR Green fluorescence. The target gene quantity was normalized with the reference gene GAPDH using the following formula, $2^{-(Ct(target)-Ct(reference))}$.

Immunochemistry analysis was performed as follows. Fixed cells were permeabilized with 1% Triton X-100, blocked with 1% bovine serum albumin, and incubated first with primary antibodies overnight at 4° C. and then with secondary antibodies for 1 hour at 37° C. The primary antibody used was mouse anti-inducible nitric oxide synthase (iNOS) (1:500, BD). The secondary antibody used for fluorescence microscopy was Alexa 594-conjugated donkey anti-mouse IgG (Molecular Probes, Carlsbad, Calif., USA), and nuclear staining was achieved using 1 μg/ml DAPI for 1 minute. For in vivo analysis, rats were perfused 7 days post-injury as described above. Samples of spinal cords including the lesion site (2 cm in length) were removed from the experimental animals. The spinal cord was longitudinally sectioned (20 μm thick) and placed on slides for inflammatory marker analysis. The primary antibodies used were goat anti-Arg I (Santa Cruz Biotechnology, Inc.), goat anti-CD206 (R&D Systems), goat anti-IL-16 (R&D Systems), mouse anti-OX42 (marker of macrophages, BD Serotec, Oxford, UK), and mouse anti-RECA-1 (marker of blood vessels, BD Serotec, Oxford, UK). The secondary antibodies used for fluorescence microscopy were Alexa 594-conjugated donkey anti-goat IgG (Molecular Probes, Carlsbad, Calif., USA), Alexa 488-conjugated donkey anti-mouse IgG (Molecular Probes, Carlsbad, Calif., USA), and Alexa 594-conjugated donkey anti-mouse IgG (Molecular Probes, Carlsbad, Calif., USA). Photographs were taken of the slides containing stained sections with a Zeiss LSM 7MP confocal microscope (Carl Zeiss, Oberkochen, Germany), and images were collected and arranged in Adobe Photoshop (Adobe Systems, Inc., San Jose, Calif., USA). The antigens of Arg I, CD206, IL-16, OX42, and RECA-1 were quantified using the NIH ImageJ 1.44d software in four longitudinal sections; three to four images were obtained through random sampling inside the epicenter area of each rat. The threshold values of antigen were maintained at constant levels in all analyzed images.

Figure 4:
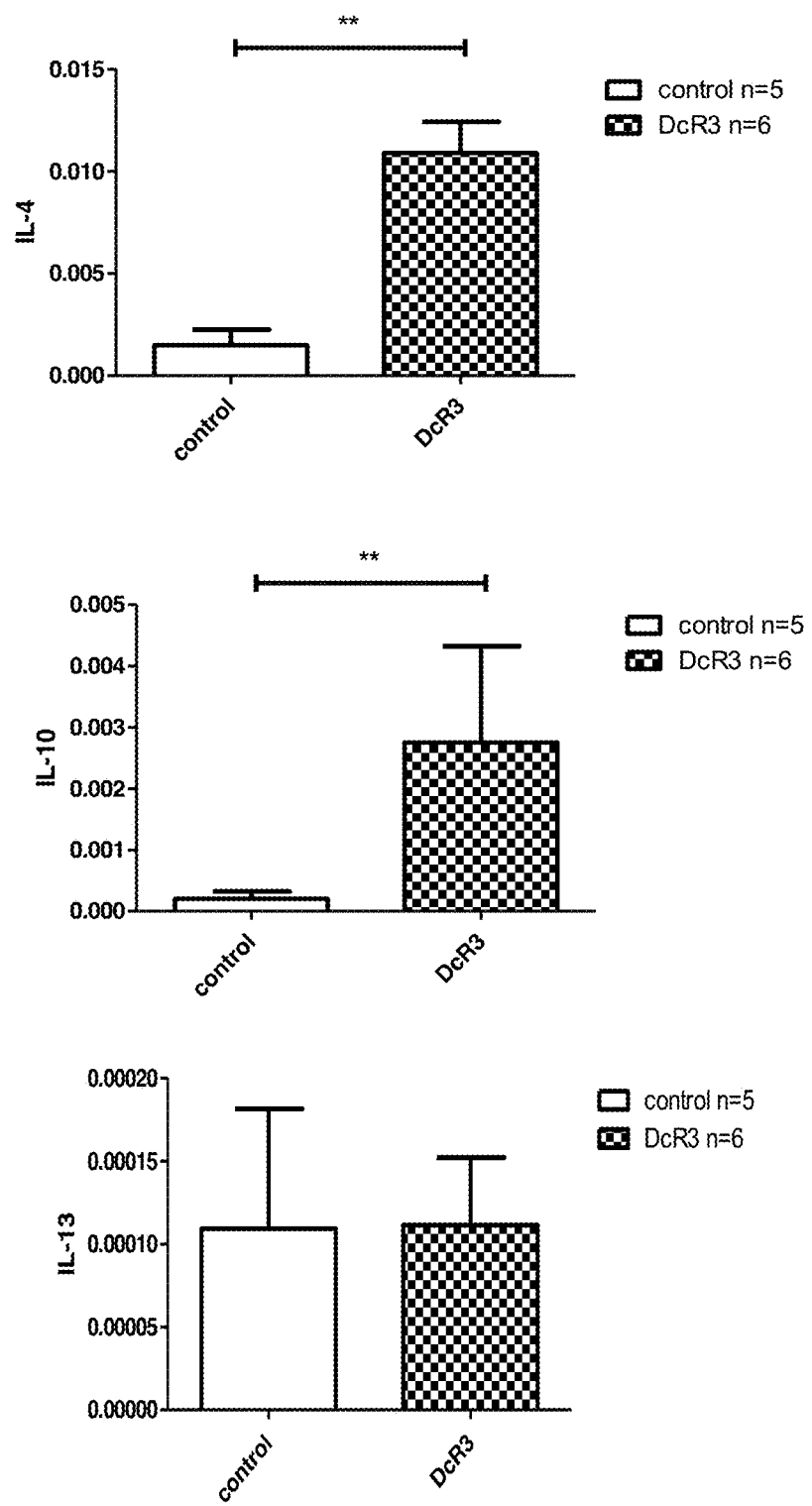
FIG. 4 provides bar graphs demonstrating that the effect of the present DcR3 treatment on the expression of anti-inflammatory cytokines, IL-4, IL-10 and IL-13; $**P<0.01$.

The results, as summarized in FIG. 4, indicate that the mRNA expressions of anti-inflammatory cytokines, including IL-4 and IL-10, were significantly elevated at the lesion sites of DcR3.Fc-treated SCI rats, suggesting that the present DcR3 treatment can modulate anti-inflammatory cytokines of SCI animals.

Figure 5A:
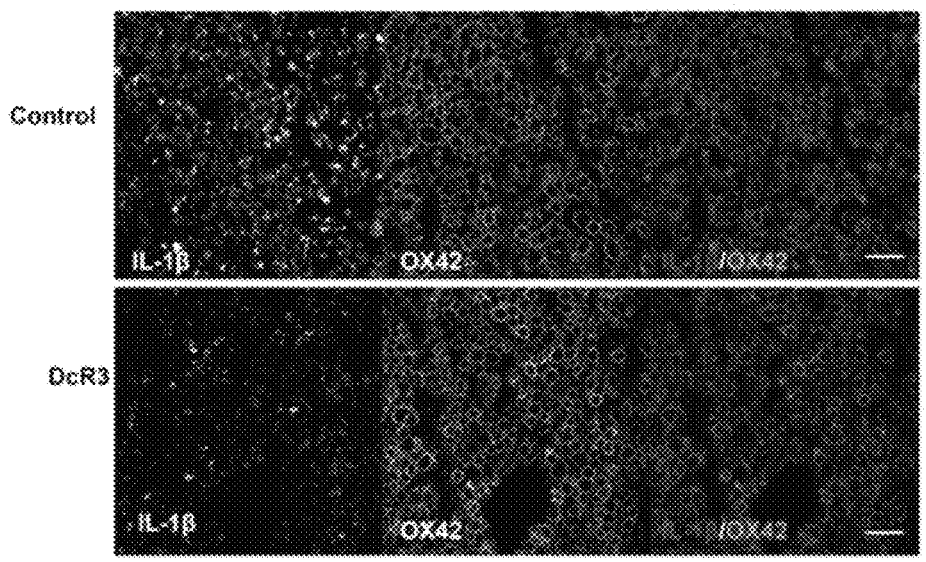
FIG. 5A provides photographs to illustrate the detection of IL-1β/OX42-positive cells in two groups by immunofluorescence staining (IL-1β, red; OX42, green; scale bar: 100 μm)
Figure 5B:
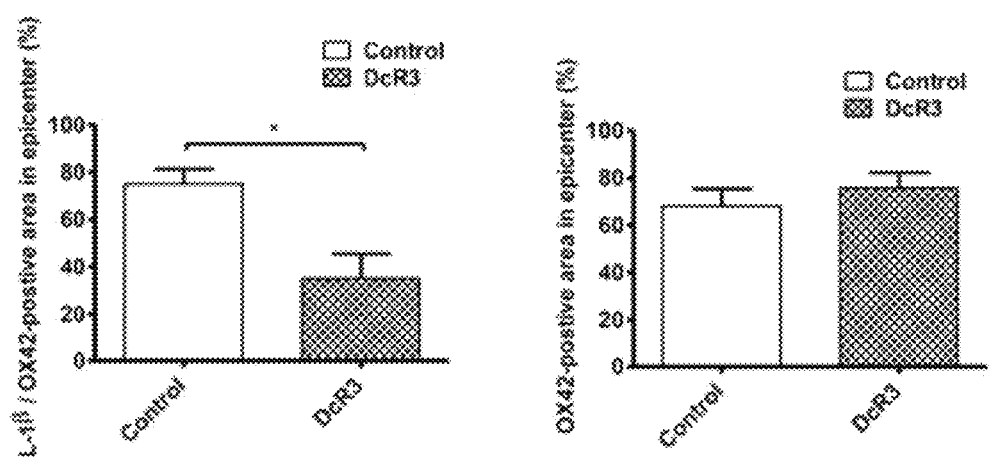
FIG. 5B provides bar graphs demonstrating the percentage of the IL-1β/OX42-positive area from the two groups in the lesion sites; $*P<0.05$.

In contrast, the expression of the pro-inflammatory cytokine IL-1β (a marker of M1 macrophage) was down-regulated at the lesion site of DcR3.Fc-treated SCI rat (see, FIG. 5A). Compared to the control group, DcR3.Fc-treated rats had a significantly lower percentage of IL-1β/OX42-positive area in the lesion sites of DcR3.Fc-treated rats at day 7 after contusion injury (FIG. 5B, left panel), even though the OX42-positive area were similar between the DcR3.Fc-treated and control groups (FIG. 5B, right panel).

Results in this Example demonstrated that DcR3.Fc is able to upregulate anti-inflammatory cytokines and down-regulate IL-16 expression in SCI animals.

Example 5

DcR3 Treatment Recruited More Alternative Activated M2 Macrophages at Lesion Sites of SCI Rats Alternatively activated M2 macrophages are involved in response and signaling to the anti-inflammatory cytokines to perform immune-resolving functions and participate in tissue repair. In this example, the expression level of gene encoding arginase I (ARGI) was used as an indicator to determine whether the present DcR3 treatment may recruit M2 macrophages at the lesion sites of SCI animals.

At 7-day post injury, spinal cord segments were homogenized in 200 mM Tris-HCl (pH 6.8), 10% Sodium dodecyl sulfate (SDS), 5 mM ethylene glycol tetraacetic acid (EGTA), 5 mM ethylenediaminetetraacetic acid (EDTA), 10% glycerol, and protease inhibitor cocktail (Sigma). Homogenates were then centrifuged at 13,000 g for 30 minutes, and the supernatants (protein extracts) were collected. Protein concentration was determined by the Bradford method (Bio-Rad protein assay, Bio-Rad Laboratories, Hercules, Calif., USA). Equal amounts (20 µg/lane) of proteins were loaded and separated by 10% sodium dodecyl sulfate polyacrylamide gel electrophoresis (SDS-PAGE). Electrophoresis was performed according to standard procedures. After electrophoresis, gels were transferred to polyvinylidene fluoride (PVDF) membranes (Millipore Corp., Billerica, Mass., USA) and blocked in phosphate buffered saline (PBS) containing 3% skim milk for 30 minutes. Each blot was than incubated overnight at 4° C. with primary antibodies against Arg I (1:1000, Santa Cruz Biotechnology Inc.) or β-actin (1:2000, Sigma). After washing in PBS, membranes were incubated with horseradish peroxidase (HRP)-conjugated secondary anti-rabbit IgG (1:5000, GE Healthcare, Arlington Heights, Ill., USA) for 2 hours, and HRP detection was performed using the enhanced chemiluminescence system.

For in vivo analysis, animals were anaesthetized using a sodium pentobarbital and were perfused intravascularly with 0.9% saline and 4% paraformaldehyde in PBS at 7-day post-injury. The spinal cords segments were collected as described above and post-fixed overnight in the same fixative at 4° C. On the following day, the fixed-cells were permeabilized with 1% Triton X-100, blocked with 1% bovine serum albumin, incubated with primary antibodies (goat anti-Arg I (Maker of M2, Santa Cruz Biotechnology Inc.); and mouse anti-OX42 (Maker of macrophage, BD Serotec, Oxford, UK)) overnight at 4° C. and secondary antibodies (Alexa 594-conjugated donkey anti-goat IgG (Molecular Probes, Carlsbad, Calif., USA), and Alexa 488-conjugated donkey anti-mouse IgG (Molecular Probes, Carlsbad, Calif., USA)) for 1 hour at 37° C. Photo images was taken from stained slides of sections with a Zeiss Axioscope microscope (Carl Zeiss, Oberkochem, Germany) and images collected and arranged in Adobe Photoshop (Adobe Systems, Inc., San Jose, Calif., USA). The antigens were quantified by NIH ImageJ 1.44d software (Wayne Rasband, National Institutes of Health, Bethesda, Md.) in four longitudinal sections included epicenter area of each rat.

Figure 6A:
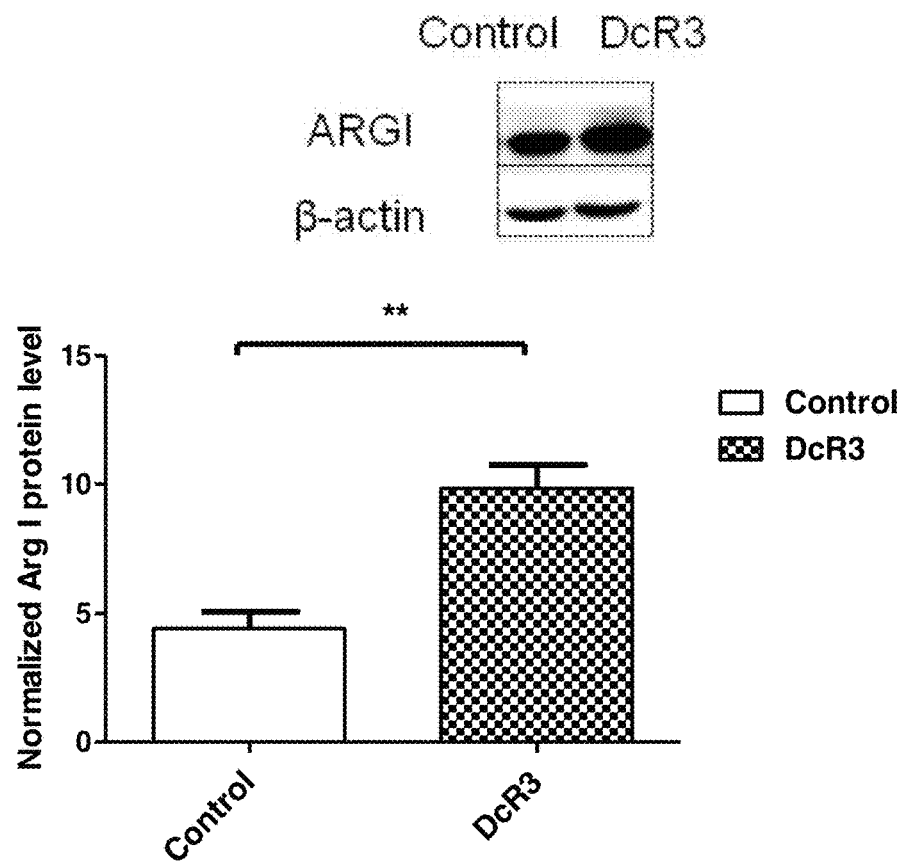
FIG. 6A and FIG. 6B provide results of Western blot analysis, which demonstrate that M2 macrophage marker ARG1 is overexpressed at lesion sites of SCI rats with the present DcR3 treatment, as determined by Western blot analysis; $*P<0.05$.
Figure 6B:
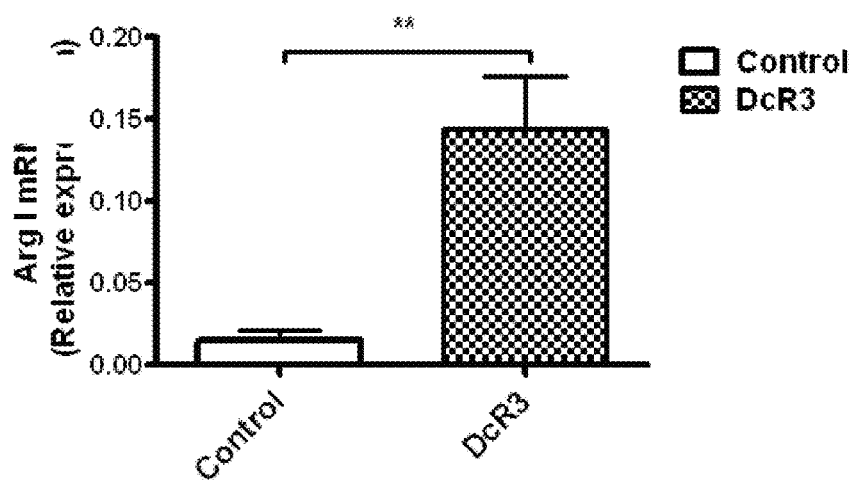
Figure 6C:
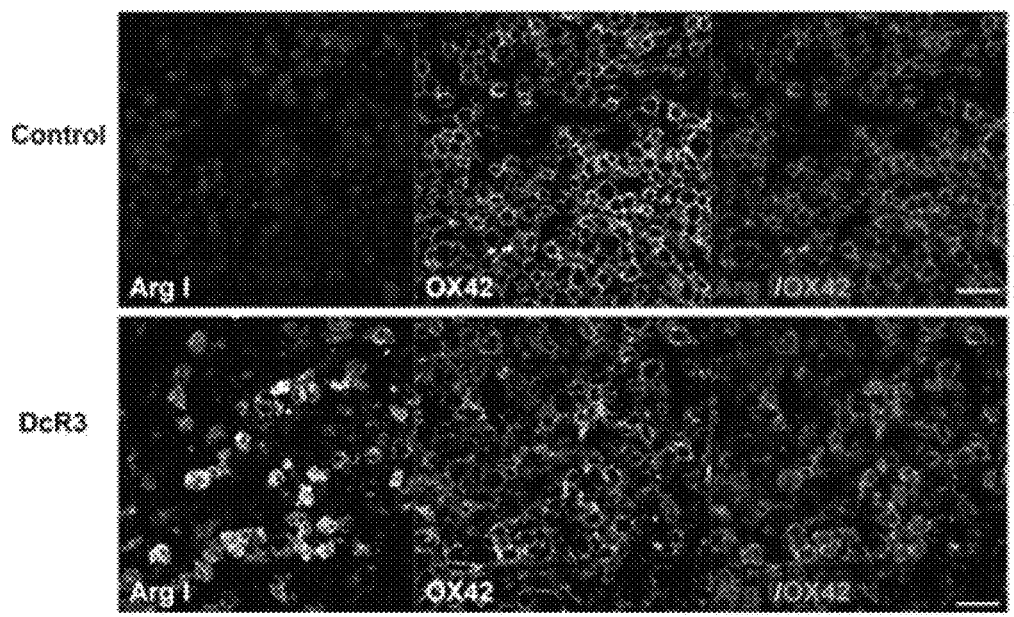
FIG. 6C to FIG. 6F are provided to demonstrate that M2 macrophage marker ARG1 is overexpressed at lesion sites of SCI rats with the present DcR3 treatment, as determined by immunofluorescence (scale bar: 100 mm); $*P<0.05$, $**P<0.01$.
Figure 6D:
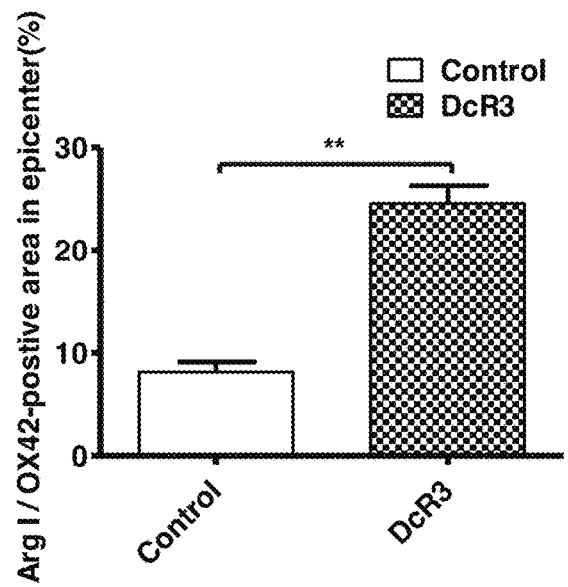
Figure 6E:
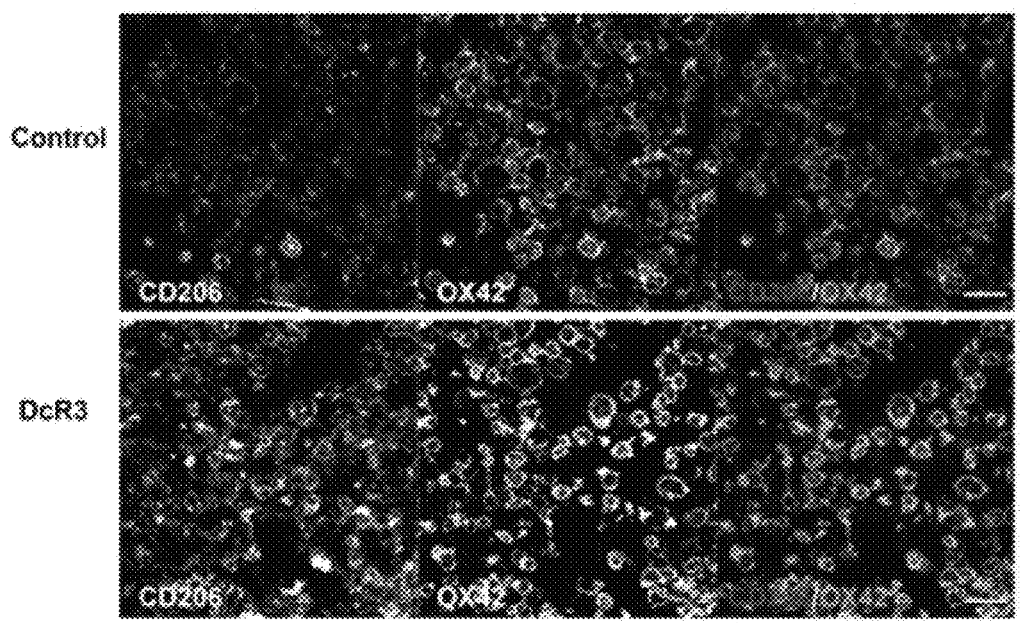
Figure 6F:
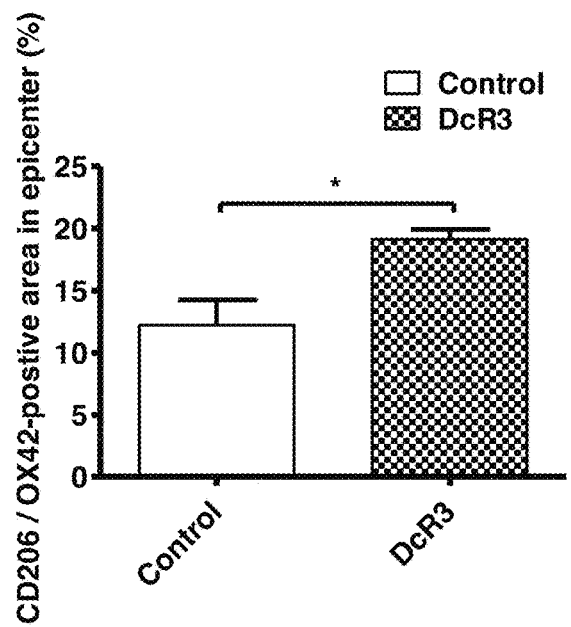

The results, as summarized in FIG. 6A to FIG. 6F indicated that the upregulated Arg I expression was observed at the lesion sites of DcR3-treated SCI rats on day 7 after contusion injury, as determined by Western blot and qPCR analyses (FIGS. 6A and 6B). Immunofluorescence staining of Arg I was increased and co-localized with OX42 (microglia/macrophage marker) in DcR3-treated rats (FIG. 6C). In addition, CD206 (M2 marker) was also co-localized with OX42-positive cells (FIG. 6E, left). Compared with the control, DcR3.Fc-treated rats had significantly higher ratios of Arg O/OX42 and CD206/OX42-positive areas in the lesion area on day 7 after contusion injury (FIGS. 6D and 6F). These observations suggest that DcR3.Fc skewed microglia into the M2 phenotype at the lesion site after contusion injury.

Example 6

DcR3 Treatment Promotes Angiogenesis at Lesion Sites

Angiogenesis occurs following SCI and its distribution correlates with the neural regeneration after SCI. To assess a potential effect of DcR3 treatment of angiogenesis on lesion sites, the rat endothelial cell antigen-1 (RECA-1) immunostaining was performed using mouse anti-reca-1 (Maker of blood vessels, BD Serotec, Oxford, UK) as the primary antibody following the protocols set forth in Example 5, above, at 7 days after SCI.

Figure 7A:
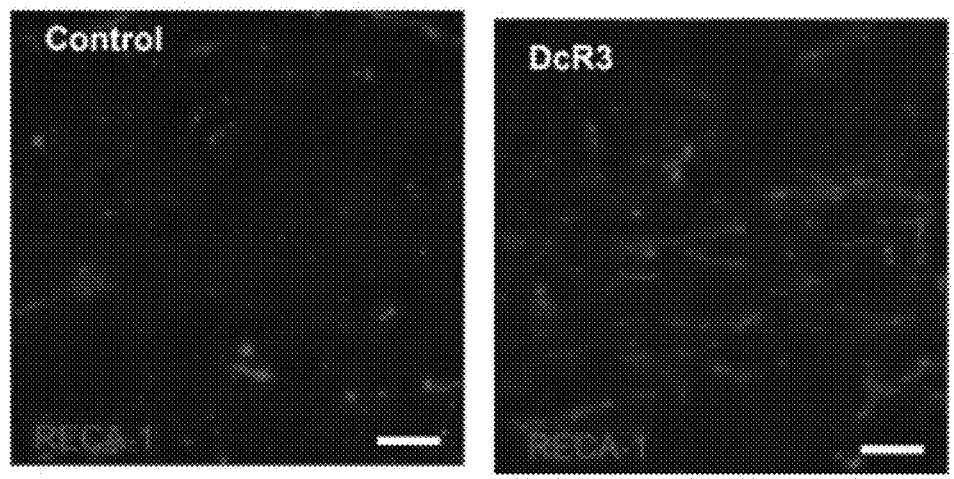
FIG. 7A and FIG. 7B are provided to demonstrate that the present DcR3 treatment promotes angiogenesis at the lesion site (n=3; scale bar: 100 mm); $*P<0.05$.
Figure 7B:
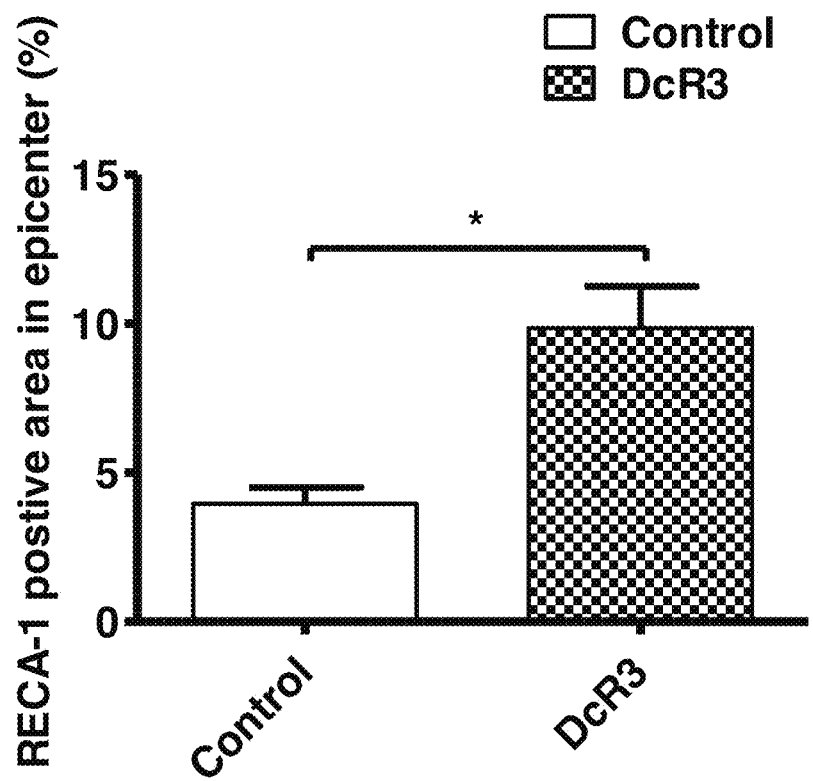

Immunohistochemistry analysis revealed a higher population of blood vessels in the epicenter of DcR3-treated cords compared to controls (FIG. 7A and FIG. 7B). This result suggests that the administration of DcR3.Fc promoted the angiogenesis at the lesion site after SCI.

Taken together, the results in Examples 1 to 5 indicate that the treatment with DcR3.Fc could promote functional recovery and result in smaller wound cavities in rats after SCI. Also, it is confirmed that DcR3.Fc is associated with an immunoregulatory activity that may induce anti-inflammatory M2 macrophages and enhance the angiogenesis after SCI. In conclusion, these results indicate beneficial effects of DcR3.Fc on SCI and suggest that DcR3.Fc can be used as a therapeutic option for SCI patients.

It will be understood that the above description of embodiments is given by way of example only and that various modifications may be made by those with ordinary skill in the art. The above specification, examples, and data provide a complete description regarding the exemplary embodiments of the present invention. Although various embodiments of the invention have been described above with a certain degree of particularity, or with reference to one or more individual embodiments, those with ordinary skill in the art could make numerous alterations to the disclosed embodiments without departing from the spirit or scope of this invention, as defined by the appended claims.

What is claimed is:

1. A method for improving the locomotor function recovery in a subject in need thereof, comprising the step of, administering to the subject an effective amount of recombinant decoy receptor 3 (DcR3) polypeptide, wherein the recombinant DcR3 polypeptide comprises, (1) a human DcR3 polypeptide fragment having the sequence identical to SEQ ID No. 1, and (2) an immunoglobulin constant region fragment (Fc region) or a fragment thereof having the sequence identical to SEQ ID No. 2.

2. The method of claim 1, wherein the subject is a rat, and the effective amount is 1 µg/kg body weight to 1 mg/kg body weight.

3. The method of claim 2, wherein the effective amount is 10 µg/kg body weight to 500 µg/kg body weight.

4. The method of claim 3, wherein the effective amount is 50 µg/kg body weight to 100 µg/kg body weight.

5. The method of claim 1, wherein the subject is a human, and the effective amount is 0.15 µg/kg body weight to 250 µg/kg body weight.

6. The method of claim 5, wherein the effective amount is 1 µg/kg body weight to 100 µg/kg body weight.

7. The method of claim 6, wherein the effective amount is 5 µg/kg body weight to 50 µg/kg body weight.

8. The method of claim 1, wherein the recombinant DcR3 polypeptide is administered via injection.

9. The method of claim 8, wherein the recombinant DcR3 polypeptide is administered via intraspinal injection.

* * * * *